United States Patent [19]

van der Meulen

[11] 4,013,922
[45] Mar. 22, 1977

[54] SUNLAMP DEVICE

[75] Inventor: Andries van der Meulen, Drachten, Netherlands

[73] Assignee: U.S. Philips Corporation, New York, N.Y.

[22] Filed: July 10, 1975

[21] Appl. No.: 594,589

[30] Foreign Application Priority Data

Aug. 1, 1974 Netherlands .................. 7410336

[52] U.S. Cl. .................. 315/362; 315/120; 315/129; 315/264; 315/340; 315/360

[51] Int. Cl.² .................. H05B 41/19; H05B 41/36

[58] Field of Search .............. 315/58, 60, 119, 120, 315/124, 224, 225, 260, 261, 264, 340, 360, 362, 129, 136

[56] References Cited

UNITED STATES PATENTS 3,014,156   12/1961   Osterhammel et al. .......... 315/224
3,262,012   7/1966    Koury et al. .................. 315/119 X Primary Examiner—Eugene La Roche
Attorney, Agent, or Firm—Frank R. Trifari; Bernard Franzblau

[57] ABSTRACT

The invention relates to a sunlamp device which is provided with a high pressure mercury vapour discharge tube and with an auxiliary device for extinguishing the discharge tube with a given time delay on termination of the desired irradiation period.

According to the invention a switch connected in series with the discharge tube is shunted by a resistor having a positive temperature coefficient of resistance (PTC resistor). This ensures that after the switch has been opened on termination of the desired irradiation period the PTC resistor passes current for some time. As a result the resistance of this PTC resistor is increased, which causes the current through the discharge tube to be reduced. This finally results in an increase of the operating voltage of the discharge tube to a value higher than the available voltage, so that the tube is extinguished. This device is simpler than a known device provided with two timers.

13 Claims, 1 Drawing Figure

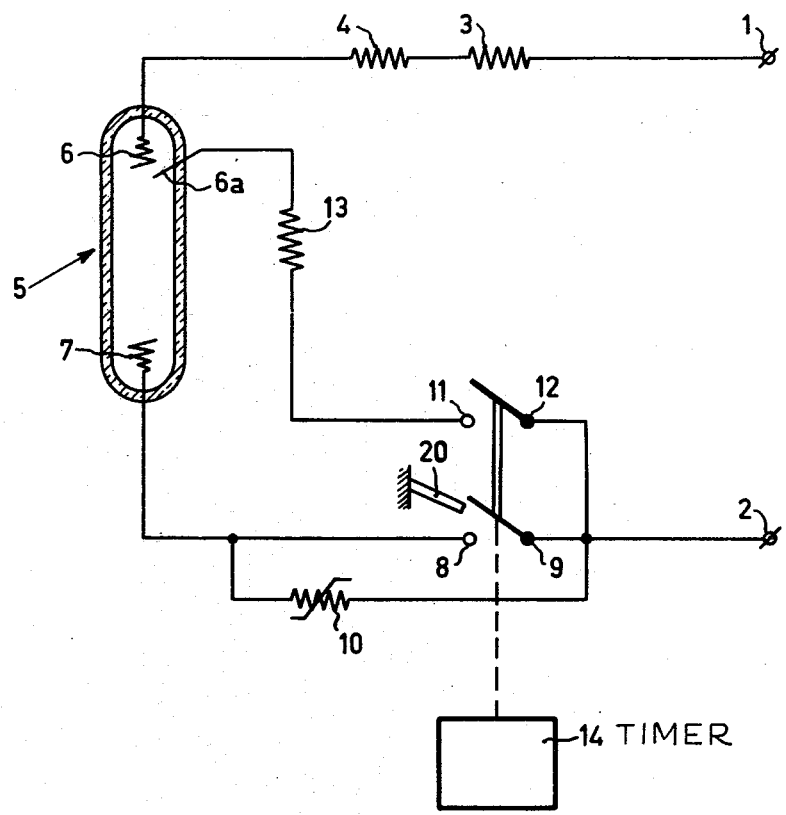

SUNLAMP DEVICE

The invention relates to a sunlamp device provided with two input terminals to which are connected a series circuit comprising a high pressure mercury vapour discharge tube provided with two electrodes and a switch which, when the discharge tube is set in operation, is set to a first position. An auxiliary device is provided for extinguishing the discharge tube with a time delay on termination of a desired irradiation period, while after extinction restriking of the discharge tube is prevented.

A known sunlamp device of the above-mentioned type is described, for example, in United Kingdom Patent 1,248,192. An advantage of this known device is that delayed extinction of the discharge tube on termination of the desired irradiation period enables the next person to sit or lay down before or under the sunlamp device in the time which elapses between the end of the desired irradiation period of the preceding person and the extinction of the discharge tube. This means that the next person can immediately start his treatment by pressing a switch button. If extinction of the discharge tube were not delayed, the second person would have to wait until the discharge tube had cooled and then had restruck.

A disadvantage of the known device is that two clocks are required, one for setting the desired irradiation period and the other for providing the extinction delay of the discharge tube. This means inter alia that the device is complicated and comparatively bulky.

It is an object of the present invention to provide an artificial sunlight device of the aforementioned type which is simple and compact but nevertheless retains the advantages with respect to delayed extinction.

A sunlamp device according to the invention is provided with two input terminals which are connected to one another by a series circuit comprising a high pressure mercury vapour discharge tube provided with two main electrodes and a switch which, when the discharge tube is set in operation, is set to a first position. An auxiliary device is provided for extinguishing the discharge tube with a time delay on termination of a desired irradiation period. After this extinction the discharge tube is prevented from restriking. The invention is characterized in that the device includes a resistor having a positive temperature coefficient of resistance which, in the first position of the switch, carries substantially no current, and in a second position of the switch the PTC resistor is in series with the discharge tube and connects the input terminals of the device to one another. The discharge tube is prevented from restriking by maintaining the voltage between the main electrodes of the discharge tube at a low value different from zero.

An advantage of this sunlamp device is that by means of a simple resistor having a positive temperature coefficient of resistance (PTC resistor) delayed extinction of the discharge tube on termination of the desired irradiation period is obtainable.

This is achieved in that on termination of the desired irradiation period the switch is set from the first position to the second position so that the current for the discharge tube is passed through the PTC resistor. This resistor, which initially is cold and consequently has a low resistance, now is traversed by a current. This means that it is heated to a temperature at which its resistance is increased. This increase of the resistance of the PTC resistor causes the current flowing through the discharge tube is reduced. As a result the operating voltage of this discharge tube exceeds the available voltage so that the tube is extinguished. The tube can be prevented from striking by various simple means. For example, the discharge tube may be shunted by a (second) resistor. In this case, in the extinguished condition of the discharge tube, the voltage across it will also be determined by the voltage division between the two resistors. If the values of the resistors are chosen so that the voltage division — of the available supply voltage — results in a voltage across the second resistor which is smaller than the striking voltage of the discharge tube, this tube will not restrike. If, afterwards, another irradiation is to be commenced, the switch will be returned to the first position. As a result the PTC resistor will be switched out of circuit so that an increased voltage is set up across the discharge tube to start it.

It should be mentioned that it is known from U.S. Pat. No. 2,967,976 to connect a discharge tube to a supply source in series with a PTC resistor. In this known device the heating of the PTC resistor reduces the current in the circuit to so small a value that the discharge tube is extinguished. However, this U.S. patent relates to a flashing light arrangement and is not concerned with the definitive extinction of the discharge tube after switching the PTC resistor into the circuit.

As mentioned hereinbefore, the discharge tube, after being extinguished, can be prevented from restriking, for example, by means of a second resistor shunting the discharge tube.

In a preferred embodiment of a device according to the invention in which the switch is shunted by the resistor having a positive temperature coefficient of resistance, the switch is coupled to a second switch in a manner such that the two switches are simultaneously opened and simultaneously closed, and the discharge tube is provided with a starting electrode which is connected to the second switch, restriking being prevented in that in the open condition of the two switches the starting electrode is switched out of circuit.

An advantage of this preferred embodiment is that restriking prevention is highly reliable. This may be explained as follows. If, for example, a sudden increase of the supply voltage occurs, the switched-off condition of the auxiliary electrode will cause the required ignition voltage between the main electrodes to be increased by an amount such that the instantaneous voltage between the main electrodes as a rule will be much too low to cause the lamp to restrike.

The first switch may be closed and opened again by the person to be irradiated.

In a further preferred embodiment of the invention the first switch is operated by a timer which on termination of the desired irradiation period sets this switch from the first position to the second position.

An advantage of the latter preferred embodiment is that with the use of only one timer and the PTC resistor, not only is the desired irradiation period obtained, but also delayed switching-off is effected.

The device may be constructed so that on termination of the desired irradiation period the tube is pivoted away. Alternatively, on termination of the desired irradiation period a shutter or screen may be moved in front of the tube to prevent the person concerned from being irradiated any longer.

In a further preferred embodiment of a device according to the invention the first switch is provided with a gong which is set into vibration by the first switch being changed over from the first to the second position.

In this preferred embodiment the person is given notice by a sound signal that his desired irradiation period is terminated and consequently that he should remove himself from the radiation. This device has the advantage of being particularly simple.

An embodiment of the invention will now be described, by way of example, with reference to the accompanying diagrammatic drawing, the single FIGURE of which is a schematic diagram of a sunlamp device according to the invention.

Referring now to the FIGURE, terminals 1 and 2 are intended to be connected to an alternating-voltage supply of about 220 volts, 50 Hz. An infrared radiator 4 is connected in series with an infrared radiator 3 to the terminal 1. The other end of the infrared radiator 4 is connected to a main electrode 6 of a high pressure mercury vapour discharge tube 5. In the operating condition the tube 5 emits ultraviolet radiation. The tube 5 is provided with another main electrode 7 and an auxiliary electrode 6a. The main electrode 7 is connected to a contact 8 of a first switch. The other contact 9 of the first switch is connected to the input terminal 2. The switch 8, 9 is shunted by a resistor 10 having a positive temperature coefficient of resistance. A second switch, the contacts of which are designated by 11 and 12, is mechanically coupled to the first switch. The contact 12 is also connected to the input terminal 2, and the contact 11 is connected via a current limiting resistor 13 to the auxiliary electrode 6a of the discharge tube 5. The two mechanically coupled switches are operated, i.e. opened, by means of a timer 14. Details of the timer and its power supply are not shown. A suitable timer is described, for example, in U.S. Pat. No. 3,909,659 (Sept. 30, 1975).

The device described operates as follows. When a person to be irradiated has taken up a position in front of the described sunlamp device, he closes the two switches 8, 9 and 11, 12, and sets the timer 14 in operation. The supply voltage of about 220 volts will then initiate an auxiliary discharge between the main electrode 6 and the auxiliary electrode 6a in the discharge tube 5, which results in a discharge being struck between the main electrodes 6 and 7. As a result, current will start flowing through the two infrared radiators 3 and 4 and through the discharge tube 5. Hence these components will irradiate the person concerned. The desired irradiation period was previously set in the timer. At the end of this period the timer 14 will open both switches simultaneously so that the main current of the discharge tube 5 will start flowing in the circuit 1, 3, 4, 5, 10, 2. As a result of PTC resistor 10, which initially had a low resistance, will achieve a high resistance by the current traversing it, so that the operating voltage of the discharge tube will exceed the available voltage and consequently the tube will be extinguished. Because the second switch has been opened at the same time as the first switch, the auxiliary electrode 6a is switched out of the circuit so that the voltage of 220 volts set up between the electrodes 6 and 7 is insufficient to cause the tube to restrike. In the interval between the end of the desired irradiation period and the instant of extinction of the discharge tube 5 the next person can take up a position in front of the device and then set the switches to the closed position (the first position). Thus he need not wait for further cooling and restriking of the discharge tube 5.

A gong 20 is struck when the first switch having contacts 8 and 9 is opened. This provides a sound signal which indicates the end of the desired irradiation period for the person concerned.

In a practical embodiment the overall resistance of the infrared radiators was about 76 ohms and the resistance of the resistor 13 was about 27 kOhms. At room temperature the resistance of the PTC resistor 10 was less than 10 ohms. About 15 seconds after the switches had been opened the resistance of the PTC resistor 10 increased to at least 100 ohms. As a result the tube 5 was extinguished. With the auxiliary electrode 6a out of circuit the starting voltage of the tube 5 was far higher than the peak value of the rated supply voltage of 220 volts. Consequently in the open position of the switches shown in the FIGURE no restriking of the tube 5 occurred after its extinction.

What is claimed is:
1. A Sunlamp device comprising two input terminals for supplying an electric current to the device, a high pressure mercury vapour discharge tube provided with two main electrodes, a switch having a first position for setting the discharge tube into operation, means connecting the discharge tube and the switch in series circuit across the input terminals, a resistor having a positive temperature coefficient of resistance thereby to extinguish the discharge tube with a time delay on termination of a desired irradiation period, said resistor of positive temperature coefficient of resistance being connected in circuit so that in the first position of the switch it carries substantially no current and in a second position of said switch said resistor is in series with the discharge tube across the input terminals of the device, and means for preventing the discharge tube from restriking after extinction thereof by maintaining the voltage between the main electrodes of the discharge tube at a low voltage different from zero.

2. A device as claimed in claim 1 wherein the switch is shunted by the resistor of positive temperature coefficient of resistance, means coupling the switch to a second switch so that the two switches are simultaneously opened and closed, the discharge tube being provided with a starting electrode connected to the second switch so that in the open position of the second switch the starting electrode is switched out of circuit thereby preventing restriking of the discharge tube.

3. A device as claimed in claim 1 further comprising a timer, the first switch being operated by said timer which on termination of the desired irradiation period changes over the switch from the first position to the second position.

4. A device as claimed in claim 3, characterized in that the first switch is provided with a gong which, on this switch being changed over from the first position to the second position, is set into vibration.

5. An irradiation apparatus comprising, a pair of input terminals for supplying an AC voltage to the apparatus, an electric discharge tube, a switch having a first operative position for energizing the discharge tube and a second position, an impedance element, means connecting the tube, the switch and the impedance element in a series circuit across the input terminals, a PTC resistor, means connecting the PTC resistor in circuit so that in the first position of said switch the PTC resistor carries substantially zero current and in the second position of the switch the PTC resistor is in series with the discharge tube across the input terminals so that a heating current flows in said PTC resistor that decreases as the resistor heats up thereby to provide a time delayed extinction of the discharge tube, said switch being switched from the first to the second position at the end of a desired irradiation period, and means coupled to the discharge tube for preventing reignition thereof.

6. An irradiation apparatus as claimed in claim 5 wherein the first circuit connecting means connects the PTC resistor in parallel with the first switch.

7. An irradiation apparatus as claimed in claim 5 wherein said reignition preventing means comprises voltage divider means including the PTC resistor and the first impedance element coupled to the input terminals so as to maintain the voltage across the discharge tube at a value below the striking voltage of the discharge tube in the second position of the switch.

8. An irradiation apparatus as claimed in claim 7 wherein the first circuit connecting means connects the PTC resistor in parallel with the first switch and said impedance element includes an infra-red radiator and said discharge tube comprises a high pressure mercury vapor tube that emits ultraviolet radiation.

9. An irradiation apparatus as claimed in claim 5 wherein the discharge tube includes a separate starting electrode, and said reignition preventing means includes a second switch coupled to the first switch so that both switches open and close in synchronism, and second means connecting the second switch in circuit with the tube starting electrode so that in the open position of the second switch the starting electrode is switched out of circuit thereby preventing reignition of the discharge tube.

10. An irradiation apparatus as claimed in claim 9 further comprising a timer coupled to said first and second switches for controlling the irradiation period, said timer operating said switches from the first position to the second position at the termination of the irradiation period, said second position of the second switch being the open position thereof.

11. An irradiation apparatus as claimed in claim 9 wherein said impedance element includes an infra-red radiator and said discharge tube comprises a high pressure mercury vapor tube that emits ultraviolet radiation.

12. An irradiation apparatus as claimed in claim 9 wherein the first circuit connecting means connects the PTC resistor in parallel with the first switch.

13. An irradiation apparatus as claimed in claim 12 wherein said second circuit connecting means connects the second switch in series with the discharge path defined by the starting electrode and one main tube electrode across the input terminals.

* * * * *

UNITED STATES PATENT AND TRADEMARK OFFICE
CERTIFICATE OF CORRECTION

PATENT NO. : 4,013,922
DATED : March 22, 1977
INVENTOR(S) : ANDRIES VAN DER MEULEN It is certified that error appears in the above-identified patent and that said Letters Patent are hereby corrected as shown below:

IN THE SPECIFICATION

Column 2, line 3, "is" should be --to be--;

Column 2, line 6, "striking" should be --restriking--.

Signed and Sealed this

Fourteenth Day of June 1977

[SEAL]

Attest:

RUTH C. MASON
*Attesting Officer*

C. MARSHALL DANN
*Commissioner of Patents and Trademarks*